United States Patent [19]

Khoobiar

[11] 4,230,640

[45] Oct. 28, 1980

[54] PROCESS FOR THE PREPARATION OF ACROLEIN AND METHACROLEIN

[75] Inventor: Sargis Khoobiar, Kinnelon, N.J.

[73] Assignee: Halcon International, Inc., New York, N.Y.

[21] Appl. No.: 847,633

[22] Filed: Nov. 1, 1977

Related U.S. Application Data

[62] Division of Ser. No. 744,657, Nov. 24, 1976, Pat. No. 4,087,382.

[51] Int. Cl.$^2$ .............................................. C07C 45/16
[52] U.S. Cl. .................................................. 568/477
[58] Field of Search ......................... 260/604 R, 603 C

[56] References Cited

U.S. PATENT DOCUMENTS

| | | |
|---|---|---|
| 3,928,462 | 12/1975 | Shiraishi et al. ................. 260/604 R |
| 4,039,583 | 8/1977 | Kawakami et al. ............. 260/604 R |
| 4,049,577 | 9/1977 | Childress et al. ................ 260/604 R |
| 4,065,507 | 12/1977 | Hardman et al. ................ 260/604 R |

Primary Examiner—Werren B. Lone
Attorney, Agent, or Firm—William C. Long; David Dick; Riggs T. Stewart

[57] ABSTRACT

A catalyst composition useful for the oxidation of olefins, particularly the oxidation of propylene and isobutylene to produce the corresponding unsaturated aldehydes acrolein and methacrolein, respectively, comprises the combination of oxides of molybdenum, cobalt, iron, bismuth, thallium and antimony, and preferably also silicon. When the catalyst is used for the vapor-phase oxidation of the olefins with molecular oxygen, the aldehydes are produced with high selectivity. Alcohol precursors for the olefins can be used as feed instead of the olefins themselves.

3 Claims, No Drawings

PROCESS FOR THE PREPARATION OF ACROLEIN AND METHACROLEIN

This is a division, of application Ser. No. 744,657 filed Nov. 24, 1976 now U.S. Pat. No. 4,087,382.

This invention relates to catalysts, and is more particularly concerned with catalysts for the vapor-phase oxidation with molecular oxygen of lower olefins to the corresponding unsaturated aldehydes of the same number of carbon atoms, and to a process for using such catalysts. The catalysts and process of this invention are particularly useful in the oxidation of propylene and isobutylene to acrolein and methacrolein, respectively.

It is well known that unsaturated aldehydes, such as acrolein and methacrolein, can be produced by the vapor-phase oxidation of the corresponding olefins by means of molecular oxygen in the presence of a suitable oxidation catalyst. A variety of catalyst compositions have been proposed for this purpose and many such compositions comprise the oxides of molybdenum, iron, bismuth, cobalt and/or nickel. As a general rule, however, the selectivity to the desired aldehyde, i.e. the molar quantity of aldehyde obtained per mole of olefin converted, has been relatively low when catalyst compositions of this type have been employed. More recently, attempts have been made to increase the selectivity of the reaction by incorporating oxides of more unusual elements in the catalyst. For example, Shiraishi et al U.S. Pat. No. 3,928,462 proposes the inclusion of thallium oxide and, optionally, the oxides of various other elements. The resultant catalyst composition makes possible increased selectivity, but substantial amounts of the olefin reacted are still converted to undesired by-products, such as carbon monoxide and carbon dioxide, so that the selectivity values still leave substantial room for improvement.

It is, accordingly, an object of this invention to provide a novel and improved catalyst composition which is effective in converting olefins to the corresponding unsaturated aldehydes with surprisingly high selectivity.

It is a further object of the invention to provide a process for converting olefins such as propylene and isobutylene to acrolein and methacrolein, respectively, with minimum formation of undesired byproducts such as carbon monoxide and carbon dioxide.

Other objects of the invention will be apparent from the following detailed description of the catalyst composition and process which characterize the invention.

It has been discovered that the desired conversion of olefins to the corresponding unsaturated aldehydes with high selectivity can be effected by carrying out the vapor-phase molecular oxidation of the olefins in the presence of a catalyst composition which comprises oxides of molybdenum, cobalt, iron, bismuth, thallium and antimony, and silicon may be optionally included. More specifically, the catalyst composition of the invention comprises the oxides of the specified elements in the following atomic ratios: Mo=12, Co=0.2–8, Fe=0.05–5, Bi=0.2–4, Tl=0.05–5, Sb=0.1–5, Si=0–20. The catalyst composition may be regarded either as a mixture of oxides of the named elements or as oxygen-containing compounds of the elements. As prepared and/or under the reaction conditions, the catalyst may contain either or both forms. The catalyst composition of the invention may then be expressed by the following general formula:

$$Mo_aCo_bFe_cBi_dTl_eSb_fSi_gO_h$$

wherein a to h indicate the atomic ratio of each component and a is 12, b is 0.2–8, c is 0.05–5, d is 0.2–4, e is 0.05–5, f is 0.1–5, g is 0–20 and h has a value which is determined by the valence and proportions of the other elements in the catalyst.

The catalyst composition is preferably used in unsupported form, e.g. in the form of pellets or other like compressed shapes of various sizes, the composition may be formed in conventional manner using techniques well known to persons skilled in the art. For example, compounds of molybdenum, cobalt, iron, thallium, antimony and bismuth are each dissolved in a small amount of water or other solvent, and the solutions are then combined and evaporated to dryness, e.g. in a rotary dryer. To prepare the catalyst the several components can be introduced into solution in the form of various salts or other compounds of convenient types and no specific form for the catalyst precursors is necessary. The use of ammonium salts, halides, e.g. chlorides, nitrates or acid forms of the elements to be supplied are, however, particularly suitable. Preferably, however, aqueous solutions are employed and water-soluble forms of the elements are used. In some cases the solutions may have acids and/or bases added to them to facilitate dissolution of the catalyst precursors. For example, acids such as hydrochloric or nitric or bases such as ammonium hydroxide can be used if desired. When silicon is to be employed as an optional component, it is suitably added in the form of an aqueous collodial solution of $SiO_2$. The resulting powder from the evaporation is then thoroughly dried and preferably screened to eliminate large particles which make it difficult to produce uniform compressed shapes, such as pellets. Typically, the powder is passed through a 20-mesh screen. The powder is then mixed with an organic binder of any conventional type, such as polyvinyl alcohol, and the mixture is thoroughly dried and again screened, typically to provide a 20-80 mesh size. The dried mixture is then preferably combined with a lubricant, again of any conventional type, such as stearic acid, and compressed into the desired shape, e.g. pelletized, or extruded or otherwise shaped, the compressed shapes typically having heights and diameters of 1/16 inch to ⅜ inch. Finally, the thus-produced catalyst composition is activated at high temperature for a prolonged period in accordance with conventional practice in this art. For example and typically, the pellets are placed in an oven or kiln, or in a tube through which air is passed, at an elevated temperature (e.g. 300°–500° C., preferably 325°–450° C.) for at least ten hours. In a particularly preferred activation step, the temperature is raised at the rate of 20° C. per hour to 400°–450° C. and this temperature is maintained for 16 hours.

It will be understood that the foregoing description regarding preparation of the catalyst in a form suitable for use in a vapor-phase oxidation reaction is merely illustrative of many possible preparative methods and is given solely by way of exemplification. This method is, however, particularly suitable and is preferred.

When the catalyst of this invention is used in the vapor-phase oxidation of olefins to form the corresponding unsaturated aldehydes, the oxidation conditions employed are those generally associated with this reaction. Thus, the reaction in which the catalyst compositions of this invention are of particular utility and in which they provide high selectivity involves contacting the appropriate olefins, e.g. propylene or isobutylene in the vapor phase with the catalyst and oxygen, preferably also in the presence of steam. Once reaction is begun, it is self-sustaining because of its exothermic nature. A variety of reactors will be found to be useful and multiple tube heat exchanger type reactors are quite satisfactory, and the process can be carried out in conventional equipment commonly employed for reactions of this type.

The gaseous feed to the reactor contains relatively low concentrations of olefin, oxygen and steam. Suitably, an inert gas, such as nitrogen, is also present. The oxygen is usually added as such or as air or as air enriched with oxygen. As mentioned, conventional oxidation conditions can be employed but, for best results, the olefin is generally present in concentrations of about 2 to 20 volume percent of the total feed with a preferred range of about 5 to 15 volume percent, and the corresponding ranges for oxygen are 4 to 20 volume percent and 5 to 15 volume percent and for steam up to 30 volume percent and 5 to 25 volume percent, the balance being the inert gas or gases.

The temperature of the reaction at the center of the reactor should, for best results, be within the range of from about 330° to 500° C., preferably 350°–200° C. and the optimum temperature range is 360° to 370° C. Because the reaction is exothermic, means for conducting the heat away from the reactor are normally employed. The temperature may be controlled by conventional methods such as by the use of reactors surrounded by a salt bath.

The pressure in the reactor is not generally critical, and the reaction may be conducted at atmospheric, superatmospheric or subatmospheric pressure. Preferably, however, pressures ranging from atmospheric up to 200 psig, preferably up to 100 psig, and most preferably up to 75 psig are employed.

The catalyst and the processes of the present invention are useful for the production of unsaturated aldehydes by oxidation with molecular oxygen of lower olefins generally. The preferred starting materials are the monoethylenically unsaturated olefins of from 3 to 4 carbon atoms. Best results have been obtained with isobutylene. Mixtures of olefins may be used.

The unsaturated aldehyde product may be recovered by a number of ways well known to those skilled in the art. For example, the aldehyde may be condensed, or scrubbed with water or other suitable solvents, followed by separation of the unsaturated aldehyde product from the scrubbing liquid. The gases remaining after the aldehyde-removal step are suitably recycled to the reaction, if desired, preferably after removal of net CO and $CO_2$ by conventional means, e.g. absorption in aqueous sodium hydroxide solution.

The features of the invention will be more readily apparent from the following specific examples of typical application. It will be understood, however, that these examples are for the purpose of illustration only and are not to be interpreted as limiting the invention.

EXAMPLE I

In 200 cc of water are dissolved 106 grams of the molybdenum salt $(NH_4)_6Mo_7O_{24}4H_2O$. Then 58 grams of $Co(NO_3)_2.6H_2O$ are dissolved in 150 cc of water, 10.1 grams of $Fe(NO_3)_3.9H_2O$ are dissolved in 50 cc of water, 13.3 grams of $Tl\,NO_3$ are dissolved 100 cc of water, 11.4 grams of $Sb\,Cl_3$ are dissolved in a mixture of 16 cc of water, 4 cc of concentrated HCl and 25 cc of ammonium hydroxide, and 24.3 grams of $Bi(NO_3)_3.5H_2O$ are dissolved in a mixture of 10 cc of water, 10 cc of concentrated nitric acid and 50 cc of ammonium hydroxide. These solutions, together with 80 grams of 30% collodial silicon dioxide, are red to a rotary dryer of 4000 cc capacity and the mixture in the dryer is evaporated to dryness at a temperature of 200° C. The resulting powder is removed from the dryer and dried in an oven at 150° C. for 18 hours. The dried powder is screened through a 20-mesh screen, a 4% aqueous solution of polyvinyl alcohol is added in sufficient quantity to make a damp mixture and this mixture is dried at 80°–90° C. for four hours. The dired mixture is then screened to 20–80 mesh, and about 5–8% of stearic acid powder is thoroughly mixed with it. The resulting mixture is then pelletized to form pellets of 3/16 inch height and diameter. The pellets are then activated in an oven by heating them gradually at a rate of 20° C. per hour to 400°–450° C. and maintaining them at this temperature for 16 hours. The activated pellets have a density of 0.95 gm/cc and the catalyst components molybdenum, cobalt, iron, thallium, antimony, bismuth and silicon are present in the atomic ratio of 12, 4, 0.5, 1, 1, 1 and 8, respectively.

A 60 cc quantity of this catalyst composition is placed in a reactor defined by a $\frac{1}{2}'' \times 45''$ stainless steel pipe, the reactor pipe being filled with 30 cc of inert filler (silicon carbide) below the catalyst bed and 50 cc of the inert filler above the catalyst bed in conventional manner to insure uniform temperature contact with the catalyst. Nitrogendiluted mixtures containing methacrolein, oxygen and steam in various proportions are fed to the reactor at a pressure slightly above atmospheric (2–4 psig), at temperatures ranging from 298° C.–308° C. and at a space velocity of about 1200 hr.$^{-1}$. The term "space velocity" is used in its conventional sense to mean liters of gas (STP) per liter of catalyst per hour. The reaction is run continuously with continuous feed and continuous withdrawal of exit gas but the exit gas is analyzed at intervals of several hours and the feed composition is in most cases varied at these intervals to give the overall effect of a series of different runs under different conditions. Analyses are carried out by means of gas chromatography and by absorption of the $CO_2$ in sodium hydroxide solution, using conventional techniques. The feed composition, the conditions of operation and the results of these experiments are set forth in the following tables, A and B. The olefin, oxygen and steam content of the feed is specified, the balance being nitrogen, the olefin and oxygen being determined on a dry basis. Experiments 1–9 represent one continuous run with each experiment indicating the analysis of feed and exit gas at each indicated time in hours from the start of the run. Experiments 10 to 19 represent another continuous run.

TABLE A

| Exp. No. | Temp. °C. | Time, hr. | Space Vol. hr.$^{-1}$ | Feed, Vol. % | | |
|---|---|---|---|---|---|---|
| | | | | $C_4H_8$ | $O_2$ | Steam |
| 1 | 370 | 280 | 3200 | 5.5 | 12.5 | 46 |
| 2 | 370 | 320 | 3200 | 5.5 | 12.5 | 51 |
| 3 | 370 | 344 | 3200 | 5.8 | 12.5 | 46 |
| 4 | 370 | 474 | 3200 | 6.0 | 12.5 | 39 |
| 5 | 370 | 498 | 3200 | 5.5 | 12.5 | 39 |
| 6 | 370 | 500 | 3200 | 6.6 | 12.5 | 42 |
| 7 | 370 | 731 | 3200 | 5.2 | 12.5 | 44 |
| 8 | 372 | 751 | 3200 | 5.4 | 12.5 | 37 |
| 9 | 364 | 1 | 4000 | 3.4 | 13.3 | 24 |

TABLE A-continued

| Exp. No. | Temp. °C. | Time, hr. | Space Vol. hr.$^{-1}$ | Feed, Vol. % $C_4H_8$ | $O_2$ | Steam |
|---|---|---|---|---|---|---|
| 10 | 368 | 3 | 4000 | 3.0 | 13.3 | 24 |
| 11 | 390 | 75 | 4000 | 2.27 | 13.3 | 24 |
| 12 | 390 | 99 | 3005 | 2.25 | 13.3 | 12 |
| 13 | 388 | 133 | 3005 | 3.12 | 13.3 | 12 |
| 14 | 390 | 153 | 3005 | 3.0 | 13.3 | 12 |

TABLE B

| Exp. No. | Conversion, % | Selectivity meth-acrolein | acetic acid | CO + $CO_2$ | Methacrolein in exit gas, mol % |
|---|---|---|---|---|---|
| 1 | 44.6 | 89.6 | 3.4 | 4.2 | 2.2 |
| 2 | 36.8 | 89.8 | 2.5 | 3.3 | 1.82 |
| 3 | 41 | 89.3 | 3.1 | 3.9 | 2.13 |
| 4 | 48.8 | 85.3 | 3.9 | 5.5 | 2.5 |
| 5 | 61.5 | 90.8 | 1.66 | 2.9 | 3.07 |
| 6 | 41.3 | 88 | 3.9 | 2.6 | 2.4 |
| 7 | 31.4 | 88.8 | 2.0 | 4.3 | 1.45 |
| 8 | 33.5 | 90.2 | 2.6 | 3.9 | 1.63 |
| 9 | 51.6 | 86 | 3.5 | 7.5 | 1.51 |
| 10 | 60.4 | 89.4 | 3.6 | 4.6 | 1.62 |
| 11 | 73.7 | 89.6 | 2.0 | 7 | 1.5 |
| 12 | 69.4 | 89.6 | 1.4 | 7.8 | 1.4 |
| 13 | 81 | 85.8 | 4.3 | 7.9 | 2.17 |
| 14 | 83.1 | 84.6 | 4.4 | 8.8 | 2.11 |

EXAMPLE 2

Example 1 is repeated except that in making the catalyst composition the amount of thallium is doubled so that the atomic relationship's among the molybdenum, cobalt, iron, thallium, antimony, bismuth and silicon are 12, 4, 0.5, 2, 1, 1 and 8, respectively. The pertinent data regarding the experiments using this catalyst for the oxidation of isobutylene are set forth in the following Tables C and D. In these experiments the charge of catalyst amounted to 90 cc.

TABLE C

| Exp. No. | Temp. °C. | Time, hr. | Space Vol. hr.$^{-1}$ | Feed, Vol. % $C_4H_8$ | $O_2$ | Steam |
|---|---|---|---|---|---|---|
| 15 | 361 | 264 | 2055 | 6.8 | 13.6 | 30 |
| 16 | 376 | 288 | 2055 | 7.8 | 13.6 | 30 |
| 17 | 360 | 368 | 2055 | 7.0 | 13.6 | 28 |
| 18 | 360 | 392 | 2055 | 7.1 | 13.6 | 31.5 |
| 19 | 370 | 416 | 2055 | 7.3 | 13.6 | 30 |
| 20 | 370 | 440 | 2055 | 7.4 | 13.6 | 31.5 |
| 21 | 370 | 464 | 2055 | 7.5 | 13.6 | 30 |

TABLE D

| Exp. No. | Conversion, % | Selectivity meth-acrolein | acetic acid | CO + $CO_2$ | Methacrolein in exit gas, mol % |
|---|---|---|---|---|---|
| 15 | 59.2 | 90.9 | 3.4 | 4.7 | 3.66 |
| 16 | 71.6 | 88.6 | 0.9 | 9.3 | 4.95 |
| 17 | 57.5 | 90.5 | 2.8 | 3.4 | 3.64 |
| 18 | 63.9 | 88.2 | 3.6 | 4.2 | 4.0 |
| 19 | 62.4 | 90 | 2.9 | 3.5 | 4.1 |
| 20 | 50.6 | 90.1 | 3.0 | 4.4 | 3.37 |

TABLE D-continued

| Exp. No. | Conversion, % | Selectivity meth-acrolein | acetic acid | CO + $CO_2$ | Methacrolein in exit gas, mol % |
|---|---|---|---|---|---|
| 21 | 69.3 | 90.4 | 2.9 | 3.3 | 4.7 |

EXAMPLE 3

Example 1 is again repeated except that in making the catalyst composition the silicon dioxide is omitted, the atomic relationships among the other components remaining the same. As in Example 2, the catalyst charge amounts to 90 cc. The data for the experiments using this catalyst are set forth in Tables E and F which follow.

TABLE E

| Exp. No. | Temp. °C. | Time, hr. | Space Vol. hr.$^{-1}$ | Feed, Vol. % $C_4H_8$ | $O_2$ | Steam |
|---|---|---|---|---|---|---|
| 22 | 366 | 5 | 2280 | 3.8 | 13.7 | 23 |
| 23 | 363 | 23 | 2290 | 3.5 | 13.7 | 21 |
| 24 | 369 | 95 | 2000 | 4.7 | 13.7 | 29 |
| 25 | 374 | 119 | 2000 | 5.1 | 13.7 | 29 |
| 26 | 380 | 143 | 2000 | 4.5 | 13.7 | 29 |

TABLE F

| Exp. No. | Conversion, % | Selectivity meth-acrolein | acetic acid | CO + $CO_2$ | Methacrolein in exit gas, mol % |
|---|---|---|---|---|---|
| 22 | 89.9 | 80.5 | 8 | 8.5 | 2.75 |
| 23 | 82.1 | 80 | 8.2 | 8.6 | 2.3 |
| 24 | 88.5 | 81 | 7.7 | 8.5 | 3.37 |
| 25 | 94 | 75 | 8.2 | 10.1 | 3.6 |
| 26 | 95.2 | 75.4 | 7.0 | 11.3 | 3.23 |

It will, of course, be understood that the alcohol precursors of the olefins, e.g. compounds which by dehydration yield the olefin, such as tertiary butyl alcohol in the case os isobutylene, can be used in place of the specified olefin. In this case the dehydration of the precursor and the oxidation of the olefin take place in the reaction zone. The following example illustrates the use of tertiary butyl alcohol in place of isobutylene to produce methacrolein by oxidation in the presence of a catalyst composition of the character described above.

EXAMPLE 4

Following the general procedure of Example 1 but using the catalyst described in Example 2 and employing tertiary butyl alcohol vapors instead of isobutylene in the feed, experiments were carried out for a total of 283 hours. In each experiment the temperature was 360° C., the space velocity was 2100 hr.$^{-1}$ and the composition of the feed gas was 11 volume of tertiary butyl alcohol, 15 volume of oxygen and 20 volume of steam, the balance being nitrogen. The time of the experiments and the results are set forth below in Table G. The conversion values are calculated on the basis of isobutylene converted since it is considered that all of the tertiary butyl alcohol is dehydrated.

TABLE G

| Exp. No. | Time, hr. | Conversion % | Selectivity meth-acrolein | acetic acid | CO + $CO_2$ | Methacrolein in exit gas, mol % | Isobutylene in exit gas, mol % |
|---|---|---|---|---|---|---|---|
| 1 | 208 | 37 | 88 | 1.7 | 4 | 3.45 | 6.6 |
| 2 | 233 | 36 | 88 | 1.7 | 5 | 2.9 | 6 |

TABLE G-continued

| Exp. No. | Time, hr. | Conversion % | Selectivity meth-acrolein | Selectivity acetic acid | $CO + CO_2$ | Meth-acrolein in exit gas, mol % | Isobutylene in exit gas, mol % |
|---|---|---|---|---|---|---|---|
| 3 | 238 | 38 | 88 | 1.45 | 5 | 3.2 | 6 |
| 4 | 260 | 45 | 90 | 1.7 | 3.8 | 4.4 | 6 |
| 5 | 261 | 40 | 90 | 1.46 | 3 | 3.6 | 6 |
| 6 | 263 | 39 | 90 | 1.5 | 3.4 | 3.4 | 6 |
| 7 | 266 | 38 | 87.5 | 1.36 | 6.2 | 3.1 | 5.7 |
| 8 | 270 | 37 | 87.5 | 1.74 | 3.8 | 3.4 | 6.7 |
| 9 | 278 | 42 | 90 | 1.57 | 2.2 | 3.9 | 6 |
| 10 | 281 | 37 | 87 | 1.47 | 3.3 | 3.5 | 6.8 |
| 11 | 283 | 34 | 90 | 1.42 | 2.3 | 3.2 | 6.8 |

The embodiments of the invention in which an exclusive property is claimed are defined as follows:

1. A process for the preparation of acrolein or methacrolein which comprises oxidizing an olefin consisting essentially of the corresponding propylene or isobutylene in the vapor-phase with molecular oxygen at a temperature in the range of from about 330° to 500° C. in the presence of a catalyst composition comprising oxides of molybdenum, cobalt, iron, bismuth, thallium, antimony and silicon, the atomic ratio of said silicon to said molybdenum being at most 20 atoms of silicon per 12 atoms of molybdenum, and said oxides of molybdenum, cobalt, iron, bismuth, thallium, antimony and silicon being integrally incorporated in said catalyst composition by intimately mixing said molybdenum, cobalt, iron, bismuth, thallium, antimony and silicon in the preparation of said catalyst composition.

2. A process as defined in claim 1, wherein the molybdenum, cobalt, iron, bismuth, thallium and antimony are present in the atomic ratios of 12, 0.2–8, 0.05–5, 0.2–4, 0.05–5 and 0.1–5 respectively.

3. A process as defined in claim 1, wherein the olefin is isobutylene and the aldehyde is methacrolein.

* * * * *